United States Patent
Skov et al.

(10) Patent No.: US 12,295,889 B2
(45) Date of Patent: *May 13, 2025

(54) SAFETY GLASSES FOR A HUMAN USER

(71) Applicant: Moldex-Metric, Inc., Culver City, CA (US)

(72) Inventors: Torben Skov, Pliezhausen (DE); Roman Skov, Stuttgart (DE)

(73) Assignee: Moldex-Metric, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/409,215

(22) Filed: Jan. 10, 2024

(65) Prior Publication Data

US 2024/0164947 A1    May 23, 2024

Related U.S. Application Data (63) Continuation of application No. 17/373,597, filed on Jul. 12, 2021, now Pat. No. 11,903,881, which is a
(Continued)

(30) Foreign Application Priority Data

Mar. 7, 2018  (EP) .................... 18160558.5

(51) Int. Cl.
*A61F 9/02* (2006.01)
*G02C 7/02* (2006.01)
(Continued)

(52) U.S. Cl.
CPC .............. *A61F 9/026* (2013.01); *A61F 9/029* (2013.01); *G02C 7/02* (2013.01); *G02C 11/00* (2013.01); *A41D 13/1184* (2013.01)

(58) Field of Classification Search
CPC . A61F 9/029; A61F 9/026; A61F 9/02; G02G 7/02; G02G 11/00; G02G 5/126; G02G 1/04; G02G 3/003; A41D 13/1184
(Continued)

(56) References Cited

U.S. PATENT DOCUMENTS 4,944,039 A   7/1990  Dietrich
5,363,153 A   11/1994 Bailiff
(Continued)

FOREIGN PATENT DOCUMENTS

DE       3617001      1/1987
DE       29721661     2/1998
(Continued)

OTHER PUBLICATIONS

"U.S. Appl. No. 16/271,722, Non Final Office Action mailed May 21, 2020", 18 pgs.
(Continued)

*Primary Examiner* — Jameson D Collier
(74) *Attorney, Agent, or Firm* — Schwegman Lundberg & Woessner, P.A.

(57) ABSTRACT

Safety glasses for a human user, with at least one lens which has an upper rim assignable to the user's forehead and a lower rim assignable to a user's cheek, with at least one nosepiece arranged at the at least one lens and with at least one protective lip to be supported on the user's face. The at least one protective lip only extends at the lower rim of the at least one lens from the at least one nosepiece towards at least one of the outer lateral rims of the lens and, in extension of the lens, downwards from the lower rim of the lens to be supported on the user's cheek.

12 Claims, 4 Drawing Sheets

Related U.S. Application Data continuation of application No. 16/271,722, filed on Feb. 8, 2019, now abandoned.

(51) Int. Cl.
  *G02C 11/00* (2006.01)
  *A41D 13/11* (2006.01)

(58) Field of Classification Search
  USPC ............................... 2/426, 435, 439, 446, 13
  See application file for complete search history.

(56) References Cited

U.S. PATENT DOCUMENTS

| | | |
|---|---|---|
| 5,506,638 A | 4/1996 | Donner |
| 5,666,182 A | 9/1997 | Donner |
| 5,666,664 A | 9/1997 | Hamilton |
| 5,697,100 A | 12/1997 | Horowitz et al. |
| 5,860,168 A | 1/1999 | Winefordner et al. |
| 11,903,881 B2 | 2/2024 | Skov et al. |
| 2004/0237962 A1 | 12/2004 | Russell |
| 2006/0082723 A1 | 4/2006 | Jamie et al. |
| 2007/0252946 A1 | 11/2007 | Welchel et al. |
| 2008/0143953 A1 | 6/2008 | Welchel et al. |
| 2008/0172778 A1 | 7/2008 | Lysogorski |
| 2008/0276356 A1 | 11/2008 | Lee |
| 2010/0257660 A1 | 10/2010 | Chou |
| 2019/0274884 A1 | 9/2019 | Skov et al. |
| 2020/0288809 A1 | 9/2020 | Skov et al. |
| 2021/0378329 A1 | 12/2021 | Skov et al. |
| 2022/0256952 A9 | 8/2022 | Skov et al. |

FOREIGN PATENT DOCUMENTS

| | | |
|---|---|---|
| EP | 0625344 | 11/1994 |
| EP | 2215997 A1 | 8/2010 |
| EP | 2215997 B1 | 8/2011 |

OTHER PUBLICATIONS

"U.S. Appl. No. 16/271,722, Response filed Oct. 13, 20 to Non Final Office Action mailed May 21, 2020", 10 pgs.

"U.S. Appl. No. 16/271,722, Final Office Action mailed Dec. 15, 2020", 16 pgs.

"U.S. Appl. No. 16/271,722, Response filed Mar. 11, 2021 to Final Office Action mailed Dec. 15, 2020", 12 pgs.

"U.S. Appl. No. 16/271,722, Advisory Action mailed Mar. 18, 2021", 4 pgs.

"U.S. Appl. No. 17/373,597, Non Final Office Action mailed Feb. 17, 2023", 12 pgs.

"U.S. Appl. No. 17/373,597, Response filed Apr. 18, 2023 to Non Final Office Action mailed Feb. 17, 2023", 10 pgs.

"U.S. Appl. No. 17/373,597, Final Office Action mailed Jul. 10, 2023", 12 pgs.

"U.S. Appl. No. 17/373,597, Response filed Sep. 6, 2023 to Final Office Action mailed Jul. 10, 2023", 7 pgs.

"U.S. Appl. No. 17/373,597, Examiner Interview Summary mailed Sep. 11, 2023", 3 pgs.

"U.S. Appl. No. 17/373,597, Advisory Action mailed Sep. 18, 2023", 3 pgs.

"U.S. Appl. No. 17/373,597, Notice of Allowance mailed Oct. 12, 2023", 8 pgs.

SAFETY GLASSES FOR A HUMAN USER

This Application is a continuation of and claims the benefit of priority to U.S. application Ser. No. 17/373,597, filed Jul. 12, 2021, which is a continuation of and claims the benefit of priority to U.S. application Ser. No. 16/271,722, filed Feb. 8, 2019, which claims the benefit of priority of European Application No. 18160558.5, file Mar. 7, 2018, each of which is incorporate by reference in their entireties.

BACKGROUND OF THE INVENTION

The invention relates to safety glasses for a human user, with at least one lens which has an upper rim assignable to the user's forehead and a lower rim assignable to a user's cheek, with at least one nosepiece arranged at the lens and with at least one protective lip to be supported on the user's face.

Furthermore, the invention relates to a safety system for a human user, the safety system having safety glasses and a respiratory mask which are configured separately and can be handled separately.

PRIOR ART

There are already known prior art safety glasses and safety systems. Safety glasses serve to protect a user's eyes against dust, chips, liquid, temperature or other products which are, in particular, produced while a work piece is being machined and which may be hurled towards the user. Typically, safety glasses have one lens or two lenses which are made of a transparent material and have the refractive index of a conventional glass pane and are therefore not able to impair the user's optics. As a matter of course, however, safety glasses having lenses with a refractive index adjusted to the user are also available.

In order to ensure that the eyes are sufficiently provided with oxygen while the safety glasses are worn and the lenses are prevented from becoming steamy, the lenses are usually kept spaced apart from the user's eyes and face. To achieve this, a nosepiece is usually provided which is permanently fixed to the lenses and positions the lenses on the user's nose such that there remains a distance to the user's eyes and the user's face, respectively. Since, in this case, the aforementioned products may nevertheless enter into the vicinity of the user's eyes between the outer rim of the respective lens and the user's face, it is known to bridge this distance by means of a protective lip.

For example, the patent specification EP 2 215 997 B1 discloses safety glasses of the generic type which have a continuous lens for both of the user's eyes as well as a protective lip which extends across the entire rim or the outer perimeter of the lens and thereby covers the area between the user's face and the lens in its entirety, so that the aforementioned products cannot enter into the vicinity of the user's eyes. In order to provide the user with sufficient oxygen nevertheless, the protective lip has a plurality of openings. Therein, the protective lip extends from the lateral rim of the lens directly towards the user's face and therefore essentially projects towards the user at a right angle with respect to the lens. As a result, the user's sig t is impaired to as small an extent as possible and the space the safety glasses require on the user's face is minimised. This ensures both wearing comfort and protective effect.

In interaction with respiratory masks, however, this may cause the problem that the space between the safety glasses and the respiratory mask is not sufficient to ensure that the user can wear both elements in a convenient/comfortable manner, More particularly, this may cause that, in use, the respiratory mask and the safety glasses constantly or temporarily clash with each other. Apart from impaired convenience for the user, this may result in the protective lip detaching from the user's face, for example, due to movements of the safety glasses.

The invention is therefore based on the object to create improved safety glasses which, particularly in interaction with a respiratory mask, improve the user's convenience while they simultaneously ensure that the user's eyes are protected against harmful products.

OBJECT OF INVENTION

The object the invention is based on is achieved by safety glasses having the features of claim 1. These safety glasses are to advantage in that their beneficial configuration ensures high user comfort as well as high operational safety and that the integration of a respiratory mask into the safety system that is formed by the safety glasses and the respiratory mask is achieved easily and without any difficulty. The space available on the user's face is used optimally and dirt particles are reliably prevented from reaching the user's eyes. To achieve this, it is provided according to the invention that the protective lip only extends at a lower rim of the lens from the nosepiece towards at least one lateral rim of the lens and, in prolongation of the lens, downwards from the lower rim of the lens to be supported on the user's cheek. Due to the fact that the protective lip essentially extends only at the lower rim of the lens, at least the upper rim area of the glasses is free from the sealing lip and allows an exchange of oxygen and/or air and prevents the lens from becoming steamy. Due to the fact that the protective lip, in prolongation of the lens, extends downwards away from the lower rim of the lens to be supported on the user's cheek, and does not vertically extend from the lens directly to the face, as has been customary so far, the resulting protective lip flatly covers the user's cheek and extends towards the area where, otherwise, a respiratory mask is arranged. Therein, the respiratory mask can be optionally placed on the protective lip, with the result that the protective lip and the respiratory mask overlap each other and that, firstly, the user's face and eyes are reliably protected and that, secondly, a reliable support of the protective lip on the user's face on the one hand, and of the respiratory mask on the user's face on the other hand, are ensured, in the latter case with interposition of the protective lip. The protective lip extends the lens downwards all the way to the user's cheek, with the result that the user and, more particularly, the user's eyes are reliably and constantly protected. In addition, the beneficial configuration of the safety glasses ensures that the lens can be arranged particularly close to the user's face. Due to the fact that the protective lip does not extend vertically from the lens toward the user's face but extends downwards in prolongation of the lens, the distance between the lens and the user's face can be minimised. This is, on the one hand, to advantage in that, for example, an air gap between the user's face and the lens is minimised in a section that is free from the protective lip, thus further increasing the user's safety and that, on the other hand, the risk of collision with a respiratory mask, possibly used at the same time, is reduced. Since the lens is arranged close to the user's face, additional space is created for the respiratory mask, with the result that the user can wear both the respiratory mask and the safety glasses in a comfortable and reliable manner.

SUMMARY OF THE INVENTION

According to a preferred refinement of the invention, it is provided that the safety glasses only have one continuous lens to protect both of the user's eyes and that the protective lip only extends at a lower rim of the lens from the nosepiece towards each of both lateral rims of the lens. This results in simple and compact safety glasses which can be produced in a cost-efficient manner and, since they comprise only a few component parts, ensure easy handling.

According to an alternative embodiment of the invention, the safety glasses have a separate lens for each of the user's eyes, wherein the nosepiece is connected to both lenses, and each case a protective lip only extends at a lower rim of each lens from the nosepiece towards the outer lateral rim of the respective lens. The safety glasses thus have two protective lips or protective lip parts each of which extends from the nosepiece to the lateral rim of the respective lens, i.e., along the lower rim and to the outer rim of the respective lens. This provides the user with the same protection and allows achieving the same advantages as described above. Depending on the production method, the production of the safety glasses is more cost-efficient because two separate lenses are provided, and it allows higher flexibility in adjusting the safety glasses to the user's face.

According to a preferred embodiment of the invention, the respective protective lip, said continuous one with a continuous lens or the two protective lips or protective lip parts with two lenses, is configured to be flatly supported on the user's cheek. This flat support improves the wearing comfort and optimises the sealing effect. Furthermore, this results in the protective lip having a large support surface for the respiratory mask.

In addition, the respective protective lip preferably has a curvature in its downward extension so that it is flatly supported on the user's cheek. As a result of the curvature, the shape of the protective lip is adjusted to the face and allows a comfortable and reliable, more particularly a sealing contact with the user's face.

Preferably, the lens has a convex curvature and the curvature of the respective protective lip is concave at least in certain sections. This results in an S-shaped contour of the safety glasses formed by the lens and the protective lip. This contour ensures, on the one hand, a beneficial support on the user's face by means of the protective lip and, on the other hand, a beneficial protection of the user's eyes.

In particular, the respective protective lip is formed integrally with the nosepiece. In the final analysis, this results in a continuous protective lip for the safety glasses, irrespective of whether the safety glasses have one lens or two lenses. In the vicinity of the nose, the protective lip is only interrupted by the shape of the nosepiece.

Preferably, the continuous protective lip contributes to forming the nosepiece. As a result, the nosepiece has a shape which corresponds to the shape of the protective lip. The beneficial configuration of the protective lip results in an automatically advantageous nosepiece which rests on the side facing away from the user's face. This results in the additional advantage that the safety glasses can be arranged particularly close to the user's face. This reduces the distance between the lenses or the lens and, for example, the user's forehead to a minimum, with the result that dirt particles are also prevented from penetrating at that point and, at the same time, an exchange of air is ensured to prevent the lenses from becoming steamy and/or to provide the eyes with oxygen.

Preferably, the nosepiece is, at least essentially, arranged on the side of the safety glasses facing away from the user's face. In this case, this is particularly irrespective of whether the protective lip contributes to forming the nosepiece or whether the nosepiece is formed integrally with or separately from the protective lip. This results in the already aforementioned advantage with respect to the minimised distance between the lens or the lenses and the user's forehead.

Furthermore, it is preferably provided that the respective protective lip is configured such that it can be elastically deformed. This results in a high wearing comfort and a reliable seal even in case of different face shapes. Furthermore, the respective protective lip preferably has a thickness that decreases towards the end facing away from the lower rim of the lens. As a result, the protective lip, for example, is tapered and facilitates, for example, supporting a respiratory mask.

According to a preferred refinement of the invention, the respective protective lip has a mask support surface facing away from the user, wherein a respiratory mask for the user can be supported on said mask support surface. Due to the mask support surface, the protective lip, for example, extends farther across the user's cheek than it would be necessary for the actual sealing function. This, however, ensures that the respiratory mask can be reliably supported on the protective lip and that the beneficial interaction between the respiratory mask and the protective lip is achieved as has already been illustrated above.

Preferably, the mask support surface has a sliding surface in order to enable relative movements between the respiratory mask and the safety glasses. To achieve this, the sliding surface is preferably adjusted to the material and/or the surface structure of the respiratory mask in order to ensure a frictional resistance that is as low as possible. This ensures that, in use, the safety glasses are prevented from being displaced in case the respiratory mask gets out of place. Furthermore, this ensures that a movement of the respiratory mask does not eliminate the sealing effect between the safety glasses and the user's face.

According to a preferred refinement of the invention, the respective protective lip is, at least essentially, configured transparent. As a result, the protective lip also extends the lens in its function, so that the user can look down even through the protective lip.

Preferably, the respective protective lip is shaped to fit to the respective lens, particularly in a substance-to-substance bond. This ensures an integral formation of the protective lip on the lens and easy handling as well as simple assembly. This particularly prevents that the protective lip can be detached from the lens during use.

The safety system according to the invention having the features recited in the claims is characterised by the configuration of the safety glasses according to the invention. This results in the already aforementioned advantages. According to a first embodiment, the respiratory mask and the safety glasses are configured such that, when being used, the respiratory mask is supported on the protective tip of the safety glasses at least in certain regions, wherein the protective lip preferably has the already aforementioned mask support surface. According to a further embodiment, the safety glasses and the respiratory mask are configured to rest on the user's face side by side, with the result that there will be no overlapping/crossover. As a result, the safety glasses and the respiratory mask each separately rest against the user's face in a sealing manner. Due to the beneficial configuration of the safety glasses, there is enough space available for the respiratory mask, with the result that the respiratory mask, if displaced by the user, is prevented from hitting against the safety glasses and thus from impairing the sealing effect, and vice versa.

BRIEF DESCRIPTION OF THE DRAWING

Other advantages and preferred features and feature combinations particularly result from the above description and from the claims. The invention will now be illustrated in more detail below by means of the drawing. In the drawing.

DETAILED DESCRIPTION OF TILE INVENTION

Figure 1:
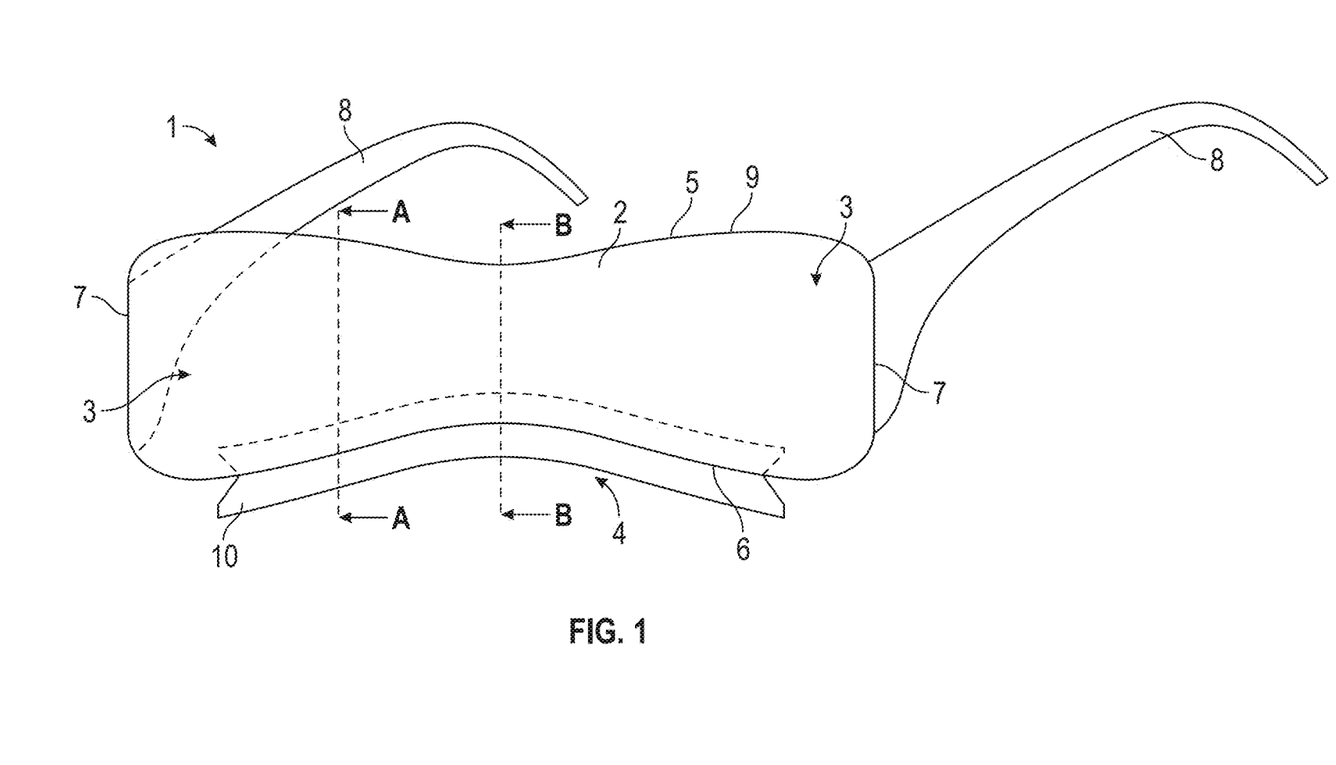
FIG. 1 is a perspective and simplified view of safety glasses for a human user.

FIG. 1 is a simplified perspective view of safety glasses 1 that are configured to be used by a human user. To achieve this, the safety glasses 1 have a lens 2 that is configured to cover both of a user's eyes. The lens 2 thus has two lens sections 3, wherein each lens section 3 can be assigned to one of the user's eyes, Between the lens sections 3, the safety glasses 1 have a nosepiece 4 which serves to support the safety glasses 1 on the user's nose and to position them on the face. The nosepiece 4 will be illustrated in more detail below. The nosepiece 4 thus rests centrally at the lens 2. The lens 2 has an upper rim 5 that can be assigned to a user's forehead, a lower rim 6 that can be assigned to the user's nose and Cheeks, with the nosepiece 4 being assigned to said lower rim 6, as well as two outer lateral rims 7 connecting the upper rim 5 to the lower rim 6. In addition, a temple 8 extending backwards from the lens 2 and towards the user's face is assigned to each of the outer lateral rims 7. The temples 8 are thus assigned to the rear side 9 of the lens 2.

Furthermore, the safety glasses 1 have a protective lip 10 that is assigned to the lower rim 6 of the lens 2. According to the present exemplary embodiment, the protective lip 10 extends almost across the entire lower rim 6 of the lens 2, Therein, the protective lip 10, at least essentially, extends across both lens sections 3 to near the respective lateral rim 7. Depending on the exemplary embodiment, the remaining distance from the lateral rim 7 can be selected larger or smaller in size, in addition, the protective lip 10 can also extend to the lateral rim 7 or beyond the latter if necessary, Due to the fact that the protective lip 10 also extends across the central area of the lens 2, the protective lip 10 extends across the nosepiece 4. According to the present exemplary embodiment, the protective lip 10 is configured such that it forms the nosepiece 4.

Figure 2:
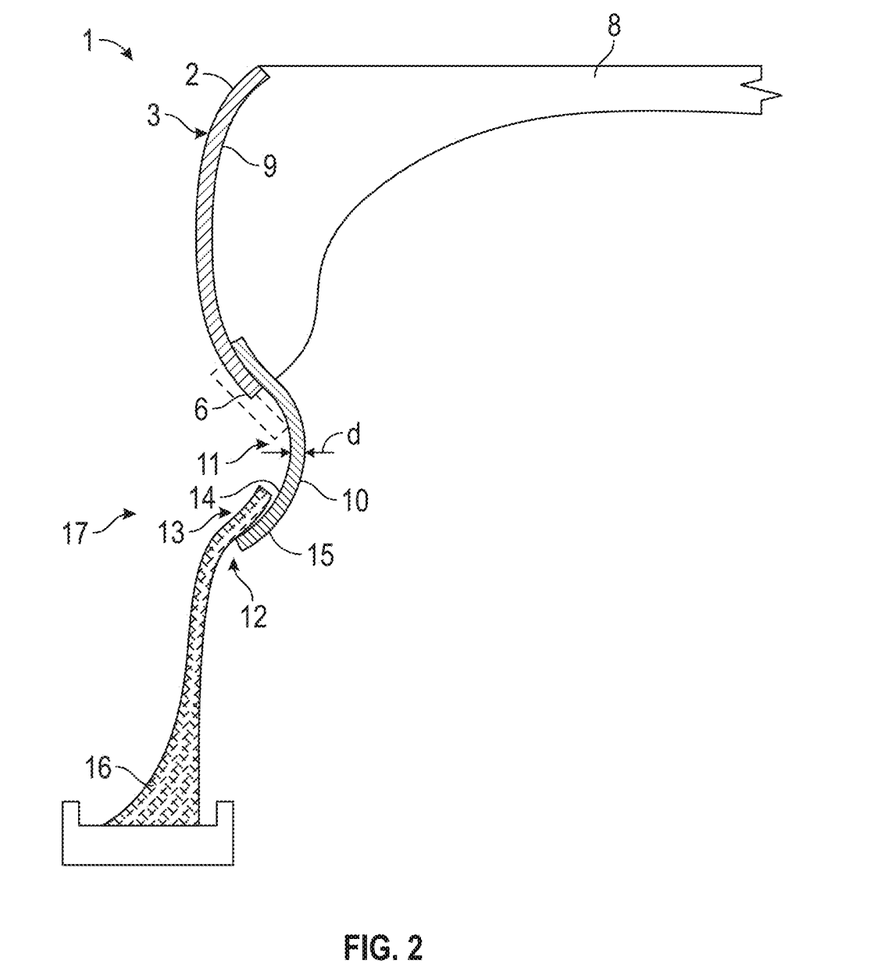
FIG. 2 is a first sectional view of the safety glasses of FIG. 1 connected with a respiratory mask.

FIG. 2 is a first sectional view of the safety glasses 1 of FIG. 1 along line A-A. The section thus rims approximately centrally through a lens section 3. The protective lip 10 is affixed to the lower rim 6. To achieve this, the protective lip 10 is, in particular, injection-moulded onto the rear side 9 of the lens 2, with the result that a substance-to-substance bond is produced between the protective lip 10 and the lens 2. While the lens 2 itself is configured transparent as is customary, the protective lip 10 can alternatively be made of a non-transparent material. According to the present exemplary embodiment, the protective lip is also made of a transparent material, Optionally, the protective lip 10 can also be made of a non-transparent material.

In particular, the protective lip 10 is configured such that it is elastically deformable; in its unloaded or non-deformed/neutral state, however, it has a curvature 11. On the one hand, the protective lip 10 is curved in its course along the lens 2 because it extends along the rim 6 on the lens 2. On the other hand, the curvature 11 of the protective lip 10 extends, as seen in cross-section, from the lens 2 down to the lower rim 6 of said lens 2, The protective lip 10 is configured such that it first follows the course of the lens 2 and finally prolongs the lens 2 at its lower rim 6. While, according to the present exemplary embodiment, the lens 2 is convex as seen from above, the protective lip 10 is concave due to the curvature 11, with the result that the lens 2 and the protective lip 10 result in an S-shape. Due to its advantageous design, the protective lip 10 is suitable to be supported on the user's cheek. In particular, the curvature 11 ensures a comfortable flat support of the protective lip 10 on the cheek which, on the one hand, ensures a high wearing comfort of the safety glasses 1 for the user and, on the other hand, a reliable seal between the lens 2 and the user's face, said seal, for example, preventing chips from reaching the user's eyes when work pieces are being machined. The protective lip 10 is configured such that it is elastically deformable, with the result that it advantageously adjusts to different face shapes and in any case provides a comfortable and reliable seal. While, according to the present exemplary embodiment, the protective lip 10 has a continuously constant thickness d, it is provided according to a further exemplary embodiment not presented here that the thickness d of the protective lip 10 decreases towards the free end 12 facing away from the lower rim 6 of the lens 2. This increases the flexibility of the protective lip 10 at its free end and even further improves the wearing comfort. Due to the filet that the protective lip 10 extends downwards in prolongation of the lens 2, the lens 2 furthermore can be arranged particularly close to the user's face; this ensures that an air gap between the lens and the user's face is minimised and that, thereby, dust or chips are prevented from entering into the area between the lens and the face, and that there is more space available for a respiratory mask on the user's face, with the result that, in particular, the respiratory mask and the safety glasses 1 are prevented from abutting against each other while they are in use and thereby, for example, from impairing the tightness of the safety glasses 1 or the respiratory mask on the user's face.

Furthermore, the protective lip 10 optionally has a mask support surface 14 on its front side 13 facing away from the user's face, particularly in the vicinity of the five end 12, wherein a support rim 15 of a respiratory mask 16 (shown with dashed lines) can be supported on said mask support surface 14. This allows an overlapping arrangement of the respiratory mask 16 and the safety glasses 1, said arrangement, on the one hand, ensuring the reliable protection of the user's eyes by means of the protective lip 10 and, on the other hand, allowing a relative movement between the safety glasses 1 and the respiratory mask 16, with the result that a movement of the safety glasses 1 or the respiratory mask 16 during use does not also result in a movement of the respiratory mask 16 or the safety glasses 1, respectively. Furthermore, the seal between the protective lip 10 and the user's face is maintained even if the respiratory mask is displaced, with the result that the operational reliability is maximised. The safety glasses 1 and the respiratory mask 16 therefore form a safety system 17 for the human user, said safety system 17, on the one hand, ensuring a high wearing comfort and, on the other hand, high operational reliability. In case of movements of the face and, more particularly, the mouth, the respiratory mask 16 also moves where applicable in order to ensure tight seating. The advantageous combination with the safety glasses 1 prevents the safety glasses 1 from also being moved or displaced thereby. In particular, the mask support surface 14 has a low roughness which ensures a low frictional adhesion between the respiratory mask 16 and the protective lip 10, with the result that an easy relative movement is enabled, Therein, the mask support surface 14 can form a section of the protective lip 10 or its surface that is different from the remaining protective lip 10. As an alternative, the protective lip 10 as a Whole has the same surface properties as on the mask support surface 14.

While, according to the present exemplary embodiment, the protective lip 10 is only affixed to the rear side 9 of the lens 2, the protective lip 10 is, according to a further exemplary embodiment which is shown by dashed lines in FIG. 2, applied, more particularly injection-moulded, both to the rear side 9 and to the front side facing away from the user, in order to ensure that the protective lip 10 is reliably held to the lens 2 even in case of higher loads.

Figure 3:
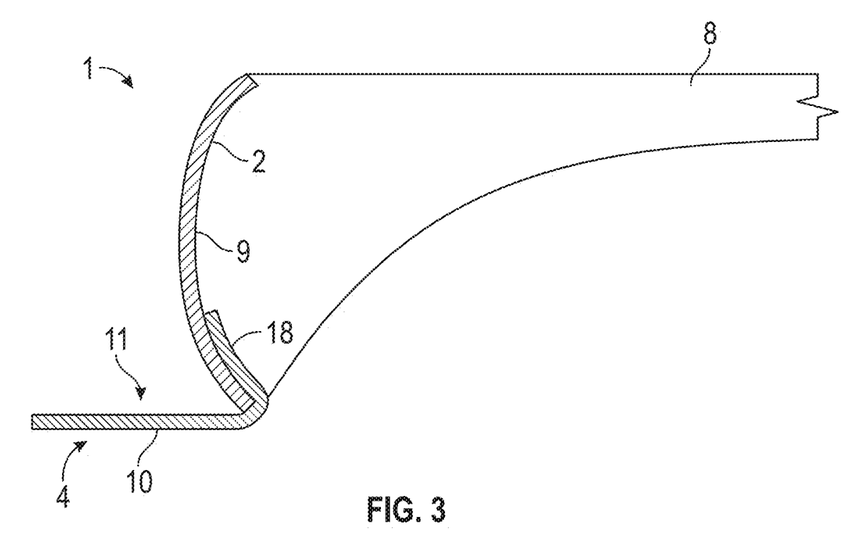
FIG. 3 is a second sectional view of the safety glasses of FIG. 1.

FIG. 3 is a second sectional view of the safety glasses 1 along Line B-B of FIG. 1 extending through the centre of the lens 2, with the result that the nosepiece is also visible in the sectional view of FIG. 3.

In the vicinity of the nosepiece 4, the protective lip 10—due to its concave curvature 11 which optionally is stronger in the vicinity of the nosepiece 4 than in the vicinity of the lens sections 3 even in the relaxed state of the protective lip 10—extends almost vertically forward from the lens 2, i.e., away from the user's face, at least when being in use. As a result, the protective lip 10 itself forms the nosepiece 4 on its rear side 18 that is facing the user. Additional means for providing a nosepiece 4 are therefore not necessary. On the one hand, the shape of the protective lip 10 in FIG. 3 can result from placing the safety glasses 1 onto the user's nose or, on the other hand, be already provided by the deformation of the protective lip 10, for example, in order to increase the wearing comfort. As a result, the nosepiece 4 is, advantageously, configured integrally with the protective lip 10.

According to an alternative exemplary embodiment that is not shown here, the nosepiece 4 can also be configured separately from the protective lip 10 or from two protective lips 10 each extending across one of the lens sections 3.

According to a further exemplary embodiment, it is provided that the lens sections are each formed by two separate lenses 2, with the result that one lens 2 is assigned to each of the user's eyes. In this case, the lenses 2 are then, for example, held together by the nosepiece 4.

Due to the fact that the nosepiece 4 extends forward away from the user's face, the respective lens 2 can be arranged particularly close to the user's face, with the result that, for example, the distance between the upper rim 5 of the lens 2 and the user's forehead is minimised as well, whereby it is ensured that the user's eyes are protected, for example, against chips at this point as well.

The integrated configuration of the protective lip 10 and the nosepiece 4 results in particularly compact safety glasses 1 that can be produced cost-efficiently and handled easily, said safety glasses 1 providing the aforementioned advantages, particularly in the safety system 17 in cooperation with the respiratory mask 16. Furthermore, the advantageous protective lip 10 allows achieving that the lens 2 as a whole can have a lower height than has been customary with previous safety glasses which seek the protection at the lower rim 6 by means of a lens 2 that extends downwards particularly far. In the case of standard safety glasses, however, this rim is comfort-restricting and cannot be flexibly adjusted to the user's face. The present beneficially configured safety glasses 1 allow providing a variety of users with comfortable reliable protection by means of only one pair of safe glasses 1. The narrower lens 2 also increases the space for the respiratory mask 16 and thereby simplifies combinations of different respiratory masks.

Figure 4:
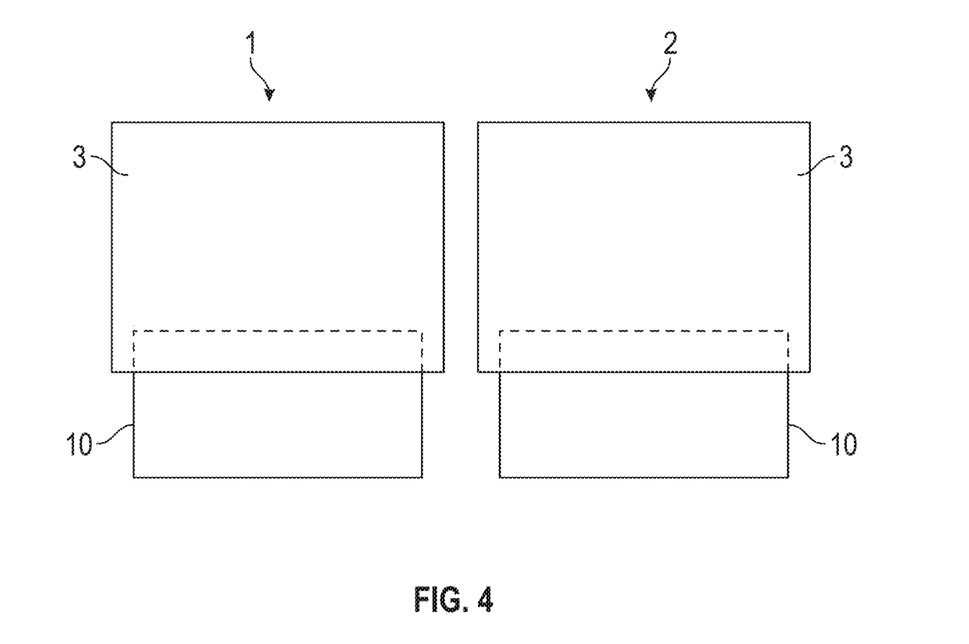
FIG. 4 is a view of a further embodiment of the safety glasses with box diagrams representing two separate lenses.

FIG. 4 shows a further embodiment of the safety glasses 1. FIG. 4 is a view of this further embodiment of the safety glasses with box diagrams representing two separate lenses. In contrast to the above described embodiment with only one lens 2 that has two lens sections 3, the lens 2 of FIG. 4 is divided into two separate lenses, one for each lens section 3.

The invention claimed is:

1. Safety glasses comprising:
   at least one lens having an upper rim and a lower rim;
   a nosepiece;
   a protective lip extending across a user's nose when the safety glasses are worn,
   wherein the protective lip extends along the lower rim of the at least one lens from the nosepiece towards an outer lateral rim of the at least one lens,
   wherein the protective lip has an upper portion having a shape corresponding to a shape of the lower rim, and
   wherein the protective lip is connected to the at least one lens in a bonding manner; and
   wherein the at least one lens has a convex curvature and a portion of the protective lip extends outwardly away from the user's cheek towards a distal free edge of the protective lip not in contact with the user's cheek when the safety glasses are worn.

2. The safety glasses of claim 1, wherein the safety glasses include a single continuous lens to protect both of the user's eyes and wherein the protective lip extends at the lower rim of the single continuous lens from the nosepiece towards both outer lateral rims of the single continuous lens.

3. The safety glasses of claim 1, wherein the safety glasses have a separate lens for each of the user's eyes, and wherein the nosepiece is connected to both lenses, and wherein the protective lip extends along the lower rim of each respective lens from the nosepiece towards the outer lateral rim of a respective lens.

4. The safety glasses of claim 1, wherein the protective lip is configured to be supported on the user's cheek when worn.

5. The safety glasses of claim 1, wherein a curvature of the protective lip is included in a downward extension of the protective lip so that the protective lip is configured to be supported on the user's cheek.

6. The safety glasses of claim 1, wherein the protective lip is integrally formed with the nosepiece.

7. The safety glasses of claim 1, wherein the protective lip forms the nosepiece.

8. The safety glasses of claim 1, wherein the protective lip is elastically deformable.

9. The safety glasses of claim 1, wherein the nosepiece is arranged on a side of the at least one lens configured to face away from the user's face when the safety glasses are worn.

10. The safety glasses of claim 1, wherein the protective lip has a mask support surface configured to face away from the user, and wherein a respiratory mask for the user can be supported on said mask support surface.

11. The safety glasses of claim 10, wherein the mask support surface has a sliding surface to facilitate relative movement between the respiratory mask and the safety glasses.

12. The safety glasses of claim 1, wherein the protective lip is transparent.

\* \* \* \* \*

UNITED STATES PATENT AND TRADEMARK OFFICE
CERTIFICATE OF CORRECTION

| | | |
|---|---|---|
| PATENT NO. | : 12,295,889 B2 | |
| APPLICATION NO. | : 18/409215 | |
| DATED | : May 13, 2025 | |
| INVENTOR(S) | : Skov et al. | |

It is certified that error appears in the above-identified patent and that said Letters Patent is hereby corrected as shown below:

In the Specification

In Column 1, Line 61, delete "sig t" and insert --sight-- therefor

In Column 2, Line 14, after "OF", insert --THE--

In Column 3, Line 18, before "each", insert --in--

In Column 3, Line 31, after "lip,", insert --i.e.,--

In Column 4, Line 61, delete "tip" and insert --lip-- therefor

In Column 5, Line 24, delete "TILE" and insert --THE-- therefor

In Column 5, Line 32, delete "eyes," and insert --eyes.-- therefor

In Column 5, Line 39, delete "Cheeks," and insert --cheeks,-- therefor

In Column 5, Line 48, delete "lens 2," and insert --lens 2.-- therefor

In Column 5, Line 54, delete "necessary," and insert --necessary.-- therefor

In Column 5, Line 61, delete "rims" and insert --runs-- therefor

In Column 6, Line 4, delete "material," and insert --material.-- therefor

In Column 6, Line 13, delete "lens 2," and insert --lens 2.-- therefor

Signed and Sealed this
Sixth Day of January, 2026

John A. Squires
*Director of the United States Patent and Trademark Office*

CERTIFICATE OF CORRECTION (continued)
U.S. Pat. No. 12,295,889 B2

In Column 6, Line 38, delete "filet" and insert --fact-- therefor

In Column 6, Line 53, delete "five" and insert --free-- therefor

In Column 7, Line 13, delete "enabled," and insert --enabled.-- therefor

In Column 7, Line 16, delete "Whole" and insert --whole-- therefor

In Column 8, Line 10, delete "safe" and insert --safety-- therefor